United States Patent [19]

Baum

[11] Patent Number: 4,573,462
[45] Date of Patent: Mar. 4, 1986

[54] RESPIRATORY SYSTEM
[75] Inventor: Marcel Baum, Vienna, Austria
[73] Assignee: Drägerwerk Aktiengesellschaft, Fed. Rep. of Germany
[21] Appl. No.: 596,620
[22] Filed: Apr. 4, 1984
[30] Foreign Application Priority Data Apr. 16, 1983 [DE] Fed. Rep. of Germany ....... 3313855

[51] Int. Cl.⁴ ............................................ A61M 16/00
[52] U.S. Cl. ........................... 128/204.25; 128/207.15; 128/205.12
[58] Field of Search .................. 128/204.25, 205.12, 128/205.14, 205.17, 910, 911, 203.14, 204.21, 207.15

[56] References Cited

U.S. PATENT DOCUMENTS

| | | | |
|---|---|---|---|
| 1,630,501 | 5/1927 | Steese | 128/204.25 |
| 2,325,049 | 7/1943 | Frye et al. | 128/204.25 |
| 2,766,753 | 10/1956 | Koch et al. | 128/205.14 |
| 3,485,243 | 12/1969 | Bird et al. | 128/204.25 |
| 4,007,737 | 2/1977 | Paluch | 128/911 |
| 4,188,946 | 2/1980 | Watson et al. | 128/910 |
| 4,245,633 | 1/1981 | Erceg | 128/205.17 |
| 4,281,652 | 8/1981 | Miller | 128/911 |

Primary Examiner—Henry J. Recla
Attorney, Agent, or Firm—McGlew and Tuttle

[57] ABSTRACT

A respiratory system comprises a breathing gas source which is connected to a feed part such as a tracheal tube connection to a closed circuit respiratory gas ventilation circuit. The gas ventilation circuit has a pressure relief connection therein. The gas feed part is connected to the breathing gas source and to the breathing gas supply through a control which controls the feed of a pulse of gas through at least one gas nozzle which is mounted to extend into the feed part at a location to form a suction area in the feed part which induces the flow of the ventilating gas through the feed part and the closed circuit respiratory gas ventilation circuit.

7 Claims, 1 Drawing Figure

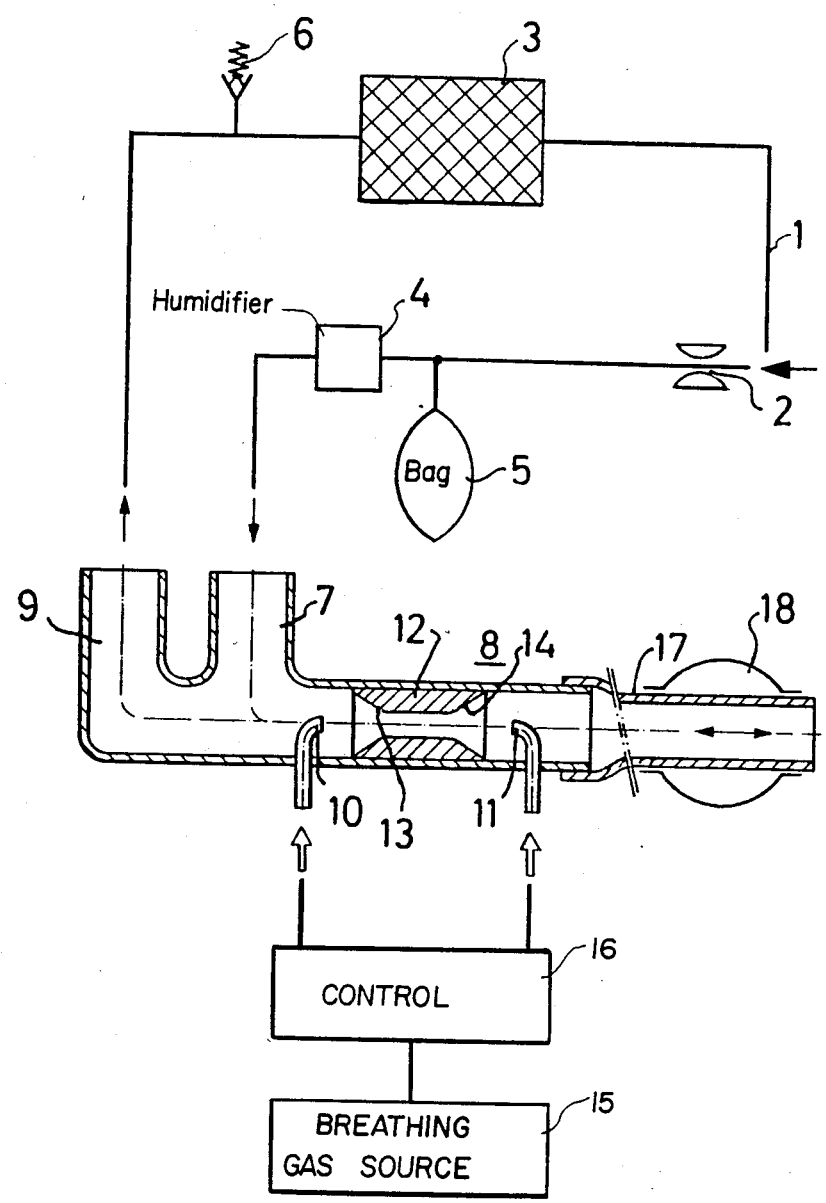

RESPIRATORY SYSTEM

FIELD AND BACKGROUND OF THE INVENTION

This invention relates in general to respirators and in particular to a new and useful respiratory system in which the flow of the ventilating gas for a closed circuit is controlled by a control member which directs gas into a feed part so as to induce the ventilating gas flow therethrough and through the closed circuit.

A respiration apparatus is known from German No. OS 31 19 814. During the inspiration phase, the jet nozzle mounted in the tracheal tube is supplied with high pressure gas pulses having a frequency which is above the natural breathing frequency, more particularly about 300 per minute. At the end of the inspiration phase, the system is switched over to the expiration phase. At the proximal end of the tracheal tube, a venturi tube is provided which is supplied from a servo gas source through an injector nozzle by which a needed underpressure is produced in the tracheal tube during the expiration phase. Such a respiration apparatus appears advantageous in that the proximal end of the tracheal tube is in permanent communication with the ambient atmosphere, so that a free exhalation is possible.

To be able to supply the necessary amount of breathing gas within the available pulse duration period, high discharge pressures at the jet nozzle and high peak loads are needed. Such high pressure jet nozzles produce considerable noise and are therefore disturbing.

The discharge effect of the jet nozzle produces a suction in the feed part, causing a displacement which may amount to a multiple of the breathing gas discharge of the jet nozzle. It is then difficult to prevent a reverse respiration without additional measures.

SUMMARY OF THE INVENTION

The invention is directed to a respiratory system which is not noisy and by which, due to the effect of the jet nozzle, the supply of a satisfactory amount of breathing gas is ensured in an open system without directional valves and while preventing reverse respiration.

In accordance with the invention a respiratory gas system comprises a breathing gas source which is connected through a control to a feed part connected in a closed circuit line which has its own pressure relief valve. The gas is directed from a supply through a control so as to discharge through a nozzle in the feed line and to create an area of suction which induces the flow of the ventilating gas.

In consequence, during the inspiration phase, due to the injector effect, breathing gas from the ventilation gas stream is taken in in addition to the jet discharge and fed into the lungs. With a circulation of 100 to 150 liters per minute, for example, and a discharge of the jet nozzle of 15 liters per minute as an average (40 liters per minute at the peak flow), a total breathing gas supply of about 80 to 120 liters per minute is obtained during the inspiration phase. In addition, the noise can effectively be damped in this arrangement without hindering the inspiration, by providing sound absorbers or the like in the system which is open at the exhalation side.

A feed part accommodating the jet nozzle is understood to comprise a connector for the tracheal tube, and/or the tracheal tube itself.

In such a respiratory system, it may be advisable to provide in the closed-circuit line an element producing the flow of the ventilation gas. Flow producing elements in lines circulating anesthetics are known, for example from U.S. Pat. No. 4,127,121. In the present case, however, the sole purpose of the flow producing element is to circulate the ventilation gas.

Advantageously, the flow producing element may be an injector nozzle supplied with breathing gas. The amount of the breathing gas introduced into the closed-circuit line through the injector nozzle depends on the amount to be used, with gas in excess escaping through the relief aperture provided in the line. This relief aperture may be provided upstream of a $CO_2$ absorber connected in the line, so that the gas in excess escapes to the outside atmosphere without loading the $CO_2$ absorber. In another advantageous embodiment, the relief aperture of the closed-circuit line may be equipped with an excess-pressure valve, so that gas is discharged into the ambient atmosphere only upon exceeding a predetermined pressure in the line.

If the relief aperture is provided in the neutral, i.e. substantially pressure-free, zone of the closed-circuit line, the aperture may advantageously remain permanently open and allow a free discharge of respiratory gas in excess, such as upon fits of coughing.

In an advantageous development, an ejector nozzle may be provided in the feed part in addition to the jet nozzle. The ejector nozzle again is supplied with breathing gas, usually by intermittently switching the breathing gas source for supplying the jet nozzle.

The arrangement of a jet nozzle and an ejector nozzle in a feed part or in a tracheal tube is an advantageous combination even in instances where no closed-circuit line is provided for circulating respiratory ventilation gas.

In various applications it is sufficient, for example, to provide the double nozzle arrangement with a jet nozzle and an ejector nozzle controlled in accordance with the respiratory cycle, in connection with a tracheal tube which is unilaterally open to the ambient atmosphere.

In an advantageous development of the invention the jet nozzle and the ejector nozzle may face each other, with their discharge directions being opposite to each other. This results in a small constructional height and a favorable orientation of the nozzles in accordance with the sought effect. In such an arrangement, the ejector nozzle is closer to the distal end of the feed part than the jet nozzle.

To decouple the two flows and augment the effect of the nozzles, it may further by advisable to provide, in the zone of the jet nozzle and/or the ejector nozzle, a flow guide converging in the flow direction. Preferably the flow guide includes two portions which converge in the discharge directions of the jet nozzle and the ejector nozzle. This ensures an independence from the diameter of the tracheal tube attached to the feed part.

The size of the jet nozzle generally corresponds to the size of the ejector nozzle, so that substantially equal discharges are obtained under equal rated pressures. By nozzles, not only conically narrowing orifices, but also free tube opening are to be understood through which a gas is discharged in a preferential direction.

The invention provides an open respiratory system silent in operation in which a satisfactory breathing gas amount in the form of high-pressure gas pulses can be supplied during the inspiration phase, without causing a reversed flow, particularly pulses having a frequency of more than 100 per minute. Moreover, an effective underpressure is produced during the expiration phase, ensuring a satisfactory removal of used-up gas components from the lungs.

Accordingly, it is an object of the invention to provide an improved respiratory gas system in which the circulation of the ventilating gas is through a feed part and into a closed circuit is controlled using a gas ejector nozzle to provide a suction in the feed part for facilitating the gas flow.

A further object of the invention is to provide a respiratory gas system which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment is illustrated.

BRIEF DESCRIPTION OF THE DRAWINGS

The only FIGURE of the drawing is a schematic sectional view of a feed part associated with a diagrammatic showing of a closed circuit line for respiratory gas constructed in accordance with the invention.

DESCRIPTION OF THE PREFERRED EMBODIMENT

Referring to the drawing in particular the invention embodied therein comprises a respiratory system which obtains breathing gas from a breathing gas supply 15 which under the control of a control member 16 directs the gas through one of two nozzles 10 and 11 in a feed part 8. Control of the breathing gas is such so as to control the ventilating gas passing through the feed part 8 and circulated through a closed circuit line 1. The nozzles 10 and 11 form a suction in their vicinity which facilitates the gas flow in a selected axial direction in the feed part 8.

The arrangement comprises a closed-circuit line 1 in which respiratory ventilation gas is circulated. This ventilation gas is supplied through an injector nozzle 2 by which the direction of circulation in line 1 is determined.

Connected in line 1 are a $CO_2$ absorber 3, a breathing air humidifier 4, and a compensation bag 5 forming the supply volume.

In the shown embodiment, the relief aperture of line 1 is closed by means of an excess pressure valve, but it may also be left entirely open.

A feed part 8 has an inlet connection 7 and an outlet connection 9 for the ventilation gas circulated in line 1.

Mounted in feed part 8 is a jet nozzle 10 and an oppositely facing ejector nozzle 11, both discharging in the axial direction. Jet nozzle 10 is so disposed that the circulated ventilation gas flows through the suction region of jet nozzle 10.

Jet nozzle 10 and ejector nozzle 11 are directed against a flow guide 12 provided therebetween and comprising portions 13 and 14 which converge in the respective discharge directions of the nozzles.

Connected to both jet nozzle 10 and ejector nozzle 11 is a breathing gas source 15 which is controllable through a control device 16 to supply high-pressure gas pulses to jet nozzle 10 during the inspiration phase, and, continuously or intermittently, breathing gas to ejector nozzle 11 during the expiration phase.

In the shown embodiment, a tracheal tube 17 equipped with a sealing sleeve 18 is connected to feed part 8.

While a specific embodiment of the invention has been shown and described in detail to illustrate the application of the principles of the invention, it will be understood that the invention may be embodied otherwise without departing from such principles.

What is claimed is:

1. A respiratory gas system, comprising a ventilating gas source, a closed circuit respiratory gas ventilating circuit connected to said ventilating gas source and having pressure relief means therein and a gas feed part connected into said gas ventilating circuit, said feed part having one end with an inlet portion and an outlet portion connected into said closed circuit respiratory gas ventilating circuit such that gas flows through said inlet portion and outlet portion, said gas feed part having a tubular intermediate portion communicating with said inlet and outlet portion, a breathing gas source first and second jet nozzles connected to said breathing gas source and extending into said tubular opposite end portion at spaced locations therein dischargeable in respective opposite axial directions to supply breathing gas into said tubular opposite end portion through said first and second jet nozzles, a patient connection means connected to said feed part at the opposite end thereof, and control means between said breathing gas source and said jet nozzles for alternately directing said breathing gas source to said jet nozzles so as to form suction areas in said feed part thereby inducing alternating, oppositely directed flows of the ventilation gas through said feed part between said closed circuit respiratory gas ventilation circuit and said patient connection means.

2. A respiratory gas system according to claim 1 wherein said jet nozzles are directed towards each other and further including a flow guide mounted in said intermediate portion between said first and second jet nozzles and having a passage therethrough converging in the flow direction of the respective nozzles and located in the vicinity of the respective nozzles.

3. A respiratory system according to claim 2, wherein said flow guide comprises a tubular member having a passage therethrough having a portion converging inwardly from each end facing a respective one of said jet nozzles.

4. A respiratory system according to claim 1, including flow producing means in said closed circuit respiratory gas ventilation circuit.

5. A respiratory system according to claim 1, wherein said flow producing means comprises an ejector nozzle connected to said ventilating gas source.

6. A respiratory system according to claim 1, including a $CO_2$ absorber in said closed circuit respiratory gas ventilation circuit.

7. A respiratory gas system according to claim 1 wherein said pressure relief means includes a relief valve for relieving excess pressure.

* * * * *